United States Patent
Nagy et al.

(10) Patent No.: US 6,759,493 B1
(45) Date of Patent: Jul. 6, 2004

(54) TRANSITION METAL CATALYSTS CONTAINING BIDENTATE LIGANDS AND METHOD OF USING AND PREPARING SAME

(75) Inventors: Sandor Nagy, Grand Island, NY (US); Leonard V. Cribbs, Liberty Township, OH (US); Bradley P. Etherton, Cincinnati, OH (US); Mary Cocoman, Grand Island, NY (US); Ramesh Krishnamurti, Williamsville, NY (US); John A. Tyrell, Williamsville, NY (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 08/872,659

(22) Filed: Jun. 10, 1997

Related U.S. Application Data

(63) Continuation-in-part of application No. 08/423,232, filed on Apr. 17, 1995, now Pat. No. 5,637,660.

(51) Int. Cl.$^7$ .............................. C08F 4/44; C08F 4/642

(52) U.S. Cl. ...................... 526/161; 526/160; 526/170; 526/172; 526/943; 502/117; 502/155; 502/103; 502/167

(58) Field of Search ................................ 526/160, 161, 526/170, 172, 103; 502/103, 117, 155, 167

(56) References Cited

U.S. PATENT DOCUMENTS

| | | | | |
|---|---|---|---|---|
| 3,900,452 A | * | 8/1975 | Valvassori et al. | 260/80.78 |
| 5,637,660 A | * | 6/1997 | Nagy et al. | 526/160 |
| 5,852,146 A | * | 12/1998 | Reichle et al. | 526/172 |

\* cited by examiner

Primary Examiner—Roberto Rabago
(74) Attorney, Agent, or Firm—Brooks Kushman P.C.

(57) ABSTRACT

Disclosed is a novel bidentate pyridine transition metal catalyst having the general formula

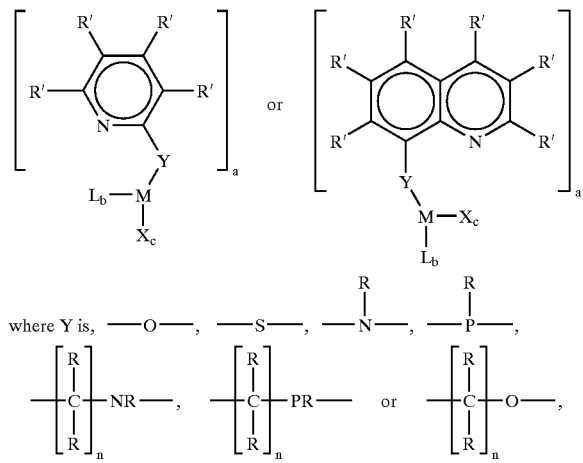

where each R is independently hydrogen, $C_{1-6}$ alkyl, or $C_{6-14}$ aryl;

where each R' is independently R, $C_{1-6}$ alkoxy, $C_{7-20}$ alkaryl, $C_{7-20}$ aralkyl, halogen, or $CF_3$;

where M is a Group 3 to 10 metal;

where each X is independently halogen, $C_{1-6}$ alkyl, $C_{6-14}$ aryl, $C_{7-20}$ alkaryl, $C_{7-20}$ aralkyl, $C_{1-6}$ alkoxy, or

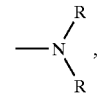

L is X, cyclopentadienyl, $C_{1-16}$ alkyl-substituted cyclopentadienyl, fluorenyl, indenyl, or

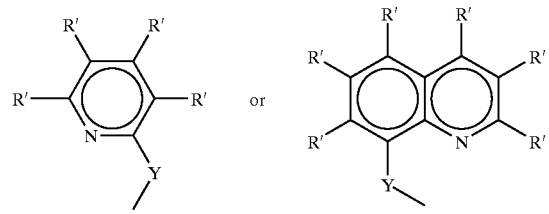

where
n is an integer from 1 to 4;
a is an integer from 1 to 3;
b is an integer from 0 to 2;
the sum of a+b≦3;
c is an integer from 1 to 6; and
the sum a+b+c equals the oxidation state of M.

44 Claims, No Drawings

TRANSITION METAL CATALYSTS CONTAINING BIDENTATE LIGANDS AND METHOD OF USING AND PREPARING SAME

This is a continuation-in-part application of U.S. patent application Ser. No. 08/423,232, filed Apr. 17, 1995 now U.S. Pat. No. 5,637,660.

BACKGROUND OF THE INVENTION

This invention relates to catalysts useful in polymerizing α-olefins. In particular, it relates to the polymerization of ethylene using transition metal catalysts with bidentate ligands containing pyridine or quinoline moieties.

Until recently, polyolefins have been made primarily using conventional Ziegler catalyst systems. A Ziegler catalyst typically consists of a transition metal-containing compound and one or more organometallic compounds. For example, polyethylene has been made using Ziegler catalysts such as titanium trichloride and diethylaluminum chloride, or a mixture of titanium tetrachloride, vanadium oxytrichloride, and triethylaluminum. These catalysts are inexpensive but they have low activity and therefore must be used at high concentrations. The catalyst residue in the polymers produce a yellow or grey color and poor ultraviolet and long term stability, and chloride-containing residues can cause corrosion in polymer processing equipment. It is therefore sometimes necessary to either remove catalyst residues from the polymer or add neutralizing agents and stabilizers to the polymer to overcome the deleterious effects of the residues and this adds to production costs. Furthermore, Ziegler catalysts produce polymers having a broad molecular weight distribution, which is undesirable for some applications such as injection molding. They are also poor at incorporating α-olefin co-monomers, making it difficult to control polymer density. Large quantities of excess co-monomer may be required to achieve a certain density and many higher α-olefins, such as 1-octene, can be incorporated at only very low levels, if at all.

Although substantial improvements in Ziegler catalyst systems have occurred since their discovery, these catalysts are now being replaced with recently discovered metallocene catalyst systems. A metallocene catalyst typically consists of a transition metal compound that has one or more cyclopentadienyl ring ligands. Metallocenes have low activities when used with organometallic compounds, such as aluminum alkyls, which are used with traditional Ziegler catalysts, but very high activities when used with aluminoxanes as cocatalysts. The activities are generally so high that catalyst residues need not be removed from the polymer. Furthermore, they produce polymers with high molecular weights and narrow molecular weight distributions. They also incorporate α-olefin co-monomers well.

However, at higher temperatures metallocene catalysts tend to produce lower molecular weight polymers. Thus, they are useful for gas phase and slurry polymerizations of ethylene, which are conducted at about 80° C. to about 95° C., but in general they do not work well as temperatures are increased. The polymerization of ethylene in solution is desirable because it allows great flexibility for producing polymers over a wide range of molecular weights and densities as well as the use of a large variety of different co-monomers. Solution polymerization permits the production of polymers that are useful in many different applications. For example, both high molecular weight, high density polyethylene (PE) film useful as a barrier film for food packaging and low density ethylene co-polymers with good toughness and high impact strength can be made.

SUMMARY OF THE INVENTION

We have discovered novel bidentate pyridine transition metal compounds which have excellent activity as α-olefin polymerization catalysts. We have also discovered that bidentate quinoline transition metal compounds, which were heretofore unsuspected of possessing any catalytic properties, are also excellent polymerization catalysts for α-olefins. These catalysts produce polymers having properties very close to the properties of polymers produced using metallocene catalysts. That is, the polymers have a narrow molecular weight distribution and a uniform co-monomer incorporation.

DESCRIPTION OF THE PREFERRED EMBODIMENTS

The transition metal catalysts of this invention containing the bidentate pyridine based ligand have the general formula

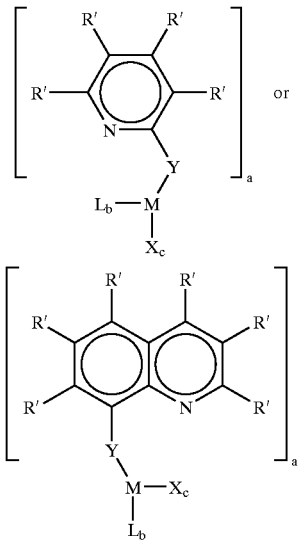

where Y is O, S, NR, PR,

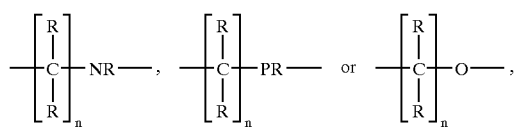

each R is independently selected from hydrogen, $C_1$ to $C_6$ alkyl, or $C_6$ to $C_{14}$ aryl, each R' is independently selected from R, $C_1$ to $C_6$ alkoxy, $C_7$ to $C_{20}$ alkaryl, $C_7$ to $C_{20}$ aralkyl, halogen, or $CF_3$, M is a Group 3 to 10 metal, each X is independently selected from halogen, $C_1$ to $C_6$ alkyl, $C_6$ to $C_{14}$ aryl, $C_7$ to $C_{20}$ alkaryl, $C_7$ to $C_{20}$ aralkyl, $C_1$ to $C_6$ alkoxy, or

L is X, cyclopentadienyl, $C_1$ to $C_6$ alkyl substituted cyclopentadienyl, indenyl, fluorenyl, or

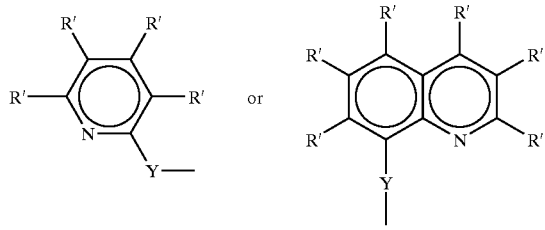

"n" is 1 to 4;
"a" is 1 to 3;
"b" is 0 to 2;
a+b≦3;
"c" is 1 to 6; and
a+b+c equals the oxidation state of M.

In the formula, the Y group is preferably oxygen as those compounds are easier to make. For the same reason the R group is preferably methyl and all of the R' are hydrogen. The L group is preferably halogen, most preferably chlorine, as those catalysts give superior properties and are easier to prepare. For the same reasons, the X group is preferably halogen, especially chlorine. The M group is preferably a Group 3 to 7 metal, most preferably a Group 4, 5 or 6 metal such as zirconium, hafnium or titanium.

In a preferred embodiment of the invention
a+b≦2 when the oxidation state of M is 4 or less; and
a+b≦3 when the oxidation state of M is greater than 4.
With the latter, a+b most preferably is less than or equal to 2 when the oxidation state of M is greater than 4.

Preparation of the bidentate pyridine complexes is illustrated in the examples, but generally they can be prepared by reacting a substituted pyridine precursor having an acidic proton with a compound having the formula $MX_3L$ in the presence of an HX scavenger. The reaction is stoichiometric and stoichiometric amounts of scavenger are preferred. Examples of suitable scavengers include compounds that are more basic than the substituted pyridine, such as triethylamine, pyridine, sodium hydride, and butyl lithium. If the scavenger is a stronger base than the substituted pyridine one can make a salt of the substituted pyridine and begin with that. While the reaction is preferably performed in a solvent, only partial solubility of the reactants is required. An aprotic solvent, such as tetrahydrofuran (THF), ether, toluene, or xylene, can be used at about 0.2 to about 20 wt% solids, and preferably at about 5 to about 10 wt% solids. The reaction can occur at about −78° C. to about room temperature. As the reaction proceeds a precipitate is formed and the product can be extracted with toluene, methylene chloride, diethyl ether, or a similar extractant.

The bidentate quinoline transition metal catalysts of this invention have the general formula

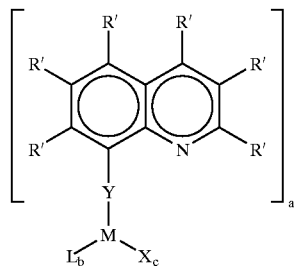

where R, R', L, M, X, "n", "a", "b" and "c" were as previously defined.

The quinoline transition metal catalysts are made in a similar manner to the pyridine transition metal catalysts except that one begins with a substituted quinoline such as 8-hydroxy quinoline (also known as 8-quinolinol) instead of the substituted pyridine. Also, butyl lithium can be used in a solvent to make the lithium salt of 8-hydroxy quinoline, which can also be used as the starting material.

The catalysts of the invention are normally used in combination with a co-catalyst. Such cocatalysts (or activators) are any compound or component which can activate the catalyst. Representative co-catalysts include alumoxanes and aluminum alkyls of the formula $Al(R_7)_3$ wherein $R^7$ independently denotes a $C_1$–$C_6$ alkyl group, hydrogen or halogen. Exemplary of the latter of such co-catalysts are triethylaluminum, trimethylaluminum and tri-isobutyl aluminum. The alumoxanes may be represented by the cyclic formulae $(R^{15}—Al—O)_g$ and the linear formula $R^{15}(R^{15}—Al—O)_s AlR^{15}$ wherein $R^{15}$ is a $C_1$–$C_5$ alkyl group such as methyl, ethyl, propyl butyl and pentyl, g is an integer from 1 to about 20 and s is about 2 to about 10. Preferably, $R^{15}$ is methyl and g is about 4. Representative but non-exhaustive examples of alumoxane co-catalysts are (poly)methylalumoxane (MAO), ethylalumoxane and diisobutylalumoxane.

The mole ratio of such co-catalysts to catalyst when used in a polymerization is generally in the range 0.01:1 to 100,000:1, and preferably ranges from 1:1 to 10,000:1.

An alternative co-catalyst is an acid salt that contains a non-coordinating inert anion (see U.S. Pat. No. 5,064,802). The acid salt is generally a non-nucleophilic compound that consists of bulky ligands attached to a boron or aluminum atom, such as lithium tetrakis(pentafluorophenyl) borate, lithium tetrakis(pentafluorophenyl)aluminate, anilinium tetrakis(pentafluorophenyl)borate, and mixtures thereof. The anion which results when these compounds react with the catalyst is believed to be weakly coordinated to the metal-containing cation. The mole ratio of acid salt to catalyst can range from about 0.01:1 to about 1000:1, but is preferably about 1:1 to 10:1. While there is no limitation on the method of preparing an active catalyst system from the catalyst and the acid salt, preferably they are mixed in an inert solvent at temperatures in the range of about −78° C. to about 150° C. They can also be mixed in the presence of monomer if desired. The acid salt can be used in combination with the above referenced cocatalysts described earlier.

The catalyst and co-catalyst can be used on a support such as silica gel, alumina, silica, magnesia, or titania, but supports are not preferred as they may leave contaminants in the polymer. However, a support may be required depending upon the process being utilized. For example, a support is generally needed in gas phase polymerization processes and slurry polymerization processes in order to control the particle size of the polymer being produced and in order to prevent fouling of the reactor walls. To use a support, the catalyst and co-catalyst are dissolved in the solvent and are precipitated onto the support material by, for example, evaporating the solvent. The co-catalyst can also be deposited on the support or it can be introduced into the reactor separately from the supported catalyst.

The catalyst is used in a conventional manner in the polymerization of olefinic hydrocarbon monomers. While unsaturated monomers such as styrene can be polymerized using the catalysts of this invention, it is particularly useful for polymerizing α-olefins such as propylene, 1-butene, 1-hexene, 1-octene, and especially ethylene.

The catalyst is also useful in a conventional manner for copolymerizing mixtures of unsaturated monomers such as ethylene, propylene, 1-butene, 1-hexene, 1-octene, and the like; mixtures of ethylene and di-olefins such as 1,3-butadiene, 1,4-hexadiene, 1,5-hexadiene, and the like; and mixtures of ethylene and unsaturated comonomers such as norbornene, ethylidene norbornene, vinyl norbornene, norbornadiene, and the like.

The catalysts of this invention can be utilized in a variety of different polymerization processes. They can be utilized in a liquid phase polymerization process (slurry, solution, suspension, bulk phase, or a combination of these), in a high pressure fluid phase, or in a gas phase polymerization process. The processes can be used in series or as individual single processes. The pressure in the polymerization reaction zones can range from about 15 psia to about 50,000 psia and the temperature can range from about −78° C. to about 300° C.

EXAMPLE 1

Synthesis of Bis(2-pyridinoxy)titanium Dichloride

To a solution of 0.02 moles of 2-hydroxy pyridine and 0.02 moles of triethylamine in 50 mL of THF, a solution of 0.01 moles of titanium tetrachloride was added dropwise at 0° C. and stirred overnight at room temperature. After filtration, the THF solution was evaporated and the product was extracted from the residue. The product has the formula:

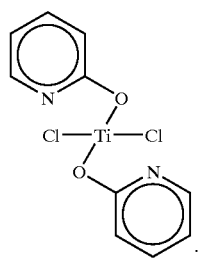

I

EXAMPLE 2

Preparation of (Cyclopentadienyl) (2-Pyridinoxy) Titanium Dichloride

To a solution of 0.002 moles of cyclopentadienyl titanium trichloride in 50 mL of ether a solution of 2-hydroxy pyridine (0.002 moles) and triethylamine (0.002 moles) in 50 mL of ether was added at 0° C. and stirred overnight. The product was recovered from the ether filtrate. The product has the formula:

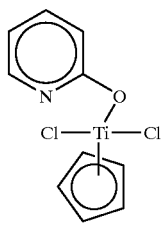

EXAMPLE 3

General Procedure For Preparation of Quinolinoxy Transition Metal Catalysts

Toluene slurries of lithium salts of various 8-quinolinol derivatives (prepared using butyl lithium) were combined with the corresponding titanium or zirconium compound (titanium tetrachloride, zirconium tetrachloride, cyclopentadienyl titanium trichloride, or cyclopentadienyl zirconium trichloride) at −78° C. and stirred overnight at room temperature. The complexes were recovered from the reaction mixture by extraction with toluene or methylene chloride. To prepare 8-quinolinoxy titanium trichloride (III)

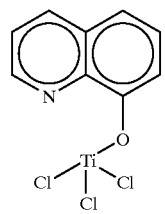

a slurry of 0.01 moles of the lithium salt of 8-hydroxyquinoline in 30 ml of toluene (prepared from 1.45 g (0.01 moles) of quinolinol and MeLi) was added at −78° C. to a solution of 1.9 g (0.01 moles) of TiCl$_4$ in 20 ml of toluene and stirred overnight at room temperature. The precipitate was separated, washed with toluene, and extracted with 100 ml of CH$_2$Cl$_2$. After the methylene chloride had been removed, a brown microcrystalline solid (0.7 g) was isolated.

Similarly, 8-(2-methyl-5,7-dichloroquinolin)oxytitanium trichloride (IV) (2.3 g)

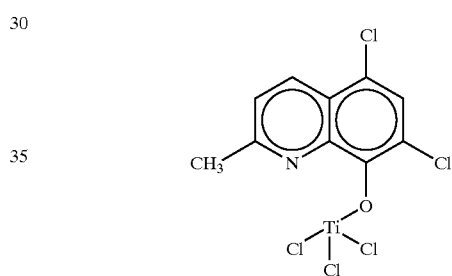

IV was prepared starting with a lithium salt made from 2.28 g (0.01 moles) of 5,7-dichloro-2-methyl-8-quinolinol.

A similar procedure was used to prepare 1.0 g of the complex bis[8-(2-methyl-5,7-dichloroquinolin)oxy]zirconiumdichloride (V)

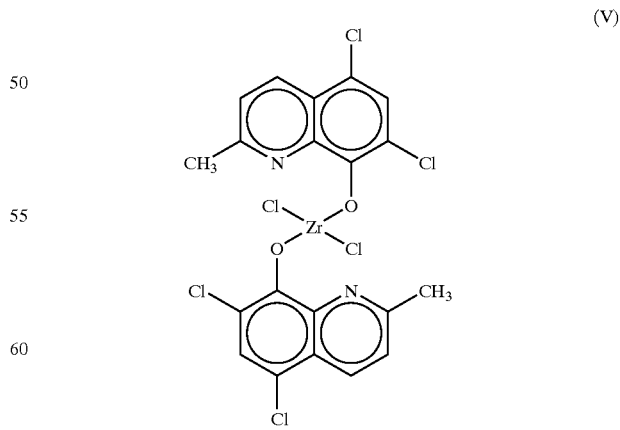

(V)

from 2.28 g (0.01 moles) of 5,7-dichloro-2-methyl-8-quinolinol and 1.165 g (0.005 moles) of zirconium tetrachloride.

To prepare (cyclopentadienyl)-(8-quinolinoxy)zirconium dichloride (VI)

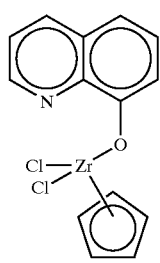

(VI)

and (cyclopentadienyl)-[8-(2-methyl-5,7-dichloroquinolin)oxy]zirconium dichloride (VII)

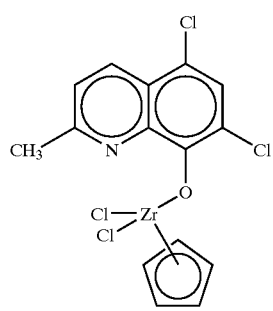

(VII)

lithium salts made from 1.45 g (0.01 moles) of 8-quinolinol or 1.15 g (0.005 moles) of 5,7-dichloro-2-methyl-8-quinolinol, respectively, were reacted with equimolar amounts of cyclopentadienyl zirconium trichloride in toluene at −78° C. After stirring overnight and filtering, the products (0.62 g of VI and 1.7 g of VII) were isolated from the toluene solution.

EXAMPLE 4

Polymerizations

All polymerizations in this study were conducted in a 1.7 L reactor. Prior to conducting a polymerization, the reactor was "baked-out" by heating to 130° C. and holding at that temperature for 30 minutes under a nitrogen purge. Ethylene, hydrogen, hexene, butene, and nitrogen were treated by passage through columns containing 13× molecular sieves. For a typical polymerization, the reactor was charged with 0.850 L of hexane or toluene and, using a syringe, the required volume of diluted PMAO (AKZO). The desired amount of hydrogen was added to the reactor by monitoring the pressure drop ($\Delta P$) from a 1 L stainless steel vessel pressurized with hydrogen. A toluene solution of catalyst was added to the reactor by nitrogen over pressure. The reactor was maintained at isothermal conditions throughout the run. Ethylene was admitted to the reactor and controlled at 150 psi with feed on demand via a pressure regulator. After the reactor temperature and pressure stabilized, the catalyst slurry was charged into the reactor and polymerization initiated. Ethylene flow was monitored via a Brooks mass flow meter.

Polymerization was terminated by venting the reactor and the polymer recovered by filtration. The polymer was stabilized by the addition of about 1000 ppm of butylated hydroxytoluene/hexane (BHT) and further devolatilized 2 hours at 80° C. in a vacuum oven. Melt flow properties of the polymer were determined in accordance with ASTM D-1238. Polymer densities were measured on compression molded samples in a density gradient column in accordance with ASTM D-1505 85.

The following table gives the reaction conditions.

| Run | Catalyst | Temp. (° C.) | Co-Monomer | Co-Monomer (grams) | Catalyst (mmoles) | Molar Ratio Al/M | H2, $\Delta P$ | Reaction Time (Min) |
|---|---|---|---|---|---|---|---|---|
| 1 | I | 80 | None | 0 | 9.5E−3 | 1897 | 0 | 15 |
| 2 | I | 80 | None | 0 | 4.7E−3 | 3795 | 0 | 15 |
| 3 | I | 80 | None | 0 | 4.7E−3 | 1897 | 20 | 15 |
| 4 | I | 80 | None | 0 | 4.7E−3 | 1897 | 50 | 10 |
| 5 | I | 80 | Butene | 20 | 4.7E−3 | 1897 | 20 | 15 |
| 6 | II | 80 | None | 0 | 9.0E−3 | 1001 | 0 | 60 |
| 7 | III | 80 | Butene | 10 | 8.4E−3 | 1074 | 10 | 30 |
| 8 | III | 80 | None | 10 | 8.4E−3 | 1074 | 10 | 30 |
| 9 | IV | 80 | Butene | 0 | 6.6E−3 | 1324 | 0 | 30 |
| 10 | IV | 80 | Butene | 10 | 6.6E−3 | 1324 | 10 | 30 |
| 11 | V | 80 | Butene | 10 | 1.14E−2 | 1175 | 0 | 10 |
| 12 | V | 80 | Butene | 10 | 4.06E−3 | 1645 | 0 | 10 |
| 13 | V | 80 | Butene | 10 | 8.12E−3 | 1645 | 0 | 10 |
| 14 | VI | 80 | Butene | 10 | 6.74E−3 | 991 | 0 | 15 |
| 15 | VI | 80 | Butene | 10 | 1.35E−2 | 991 | 0 | 15 |
| 16 | VI | 80 | Butene | 10 | 1.35E−2 | 1288 | 5 | 15 |
| 17 | VI | 80 | Butene | 10 | 1.89E−2 | 1132 | 15 | 15 |
| 18 | VI | 110 | Butene | 10 | 1.89E−2 | 1132 | 0 | 15 |
| 19 | VII | 80 | Butene | 10 | 1.10E−2 | 1212 | 0 | 15 |
| 20 | VII | 80 | Butene | 10 | 1.10E−2 | 1212 | 5 | 15 |
| 21 | VII | 110 | Butene | 10 | 1.54E−2 | 1126 | 15 | 15 |
| 22 | VII | 80 | Butene | 10 | 1.54E−2 | 1126 | 0 | 15 |
| 23 | VII | 80 | Butene | 10 | 1.54E−2 | 2078 | 0 | 15 |

In the table, "Al/M" is ratio of moles of aluminum in PMAO to moles of metal (titanium or zirconium) in the catalyst.

The following table gives the result of the polymerizations.

| Run | Catalyst Productivity (kg/gM/h) | MI2 | MI20 | MFR | Density | Mw/Mn |
|---|---|---|---|---|---|---|
| 1 | 179.0 | <0.01 | <0.01 | — | | |
| 2 | 153.2 | <0.01 | <0.01 | — | | |
| 3 | 165.5 | <0.01 | 1.8 | — | | |
| 4 | 133.1 | <0.01 | 2.47 | — | | |
| 5 | 272.9 | <0.01 | 0.964 | — | | |
| 6 | 62.9 | <0.01 | <0.01 | — | | |
| 7 | 99.2 | 0.90 | 16.9 | 18.9 | 0.9513 | 2.51 |
| 8 | 167.9 | 0.41 | 4.2 | 10.2 | 3.67 | |
| 9 | 103.2 | <0.01 | — | — | | |
| 10 | 24.8 | <0.01 | — | — | | |
| 11* | low | — | — | | | |
| 12* | none | — | — | — | | |
| 13* | none | — | — | — | | |
| 14 | none | — | — | — | | |
| 15 | 98.1 | <0.01 | 1.15 | — | | |
| 16 | 177.7 | 0.93 | 21.4 | 23.1 | | |
| 17 | 137.6 | 1.31 | 34.5 | 26.3 | | |
| 18 | 159.0 | 0.81 | 16.1 | 19.8 | | |
| 19 | 119.8 | <0.01 | .83 | — | | |
| 20 | 198.7 | 0.46 | 11.4 | 24.7 | | |
| 21 | 157.8 | 0.63 | 17.8 | 28.2 | | |
| 22 | 160.1 | 0.06 | 12.8 | — | | |
| 23 | 112.1 | 0.06 | 1.84 | 29.7 | | |

In the table, kg/gm/h is kilograms polymer produced per gram of catalyst per hour. The melt index of the polymer was measured according to ASTM D-1238, Condition E and Condition F. MI2 is the melt index measured with a 2.16 kg weight (Condition E). MI20 is the melt index measured with a 21.6 kg weight (Condition F). MFR is the ratio of MI20 to MI2. The polymer density was measured according to ASTM D-1505. The molecular weight distribution of the polymer was measured using a Waters 150C. gel permeation chromatograph at 135° C. with 1,2,4-dichlorobenzene as the solvent. Both weight average molecular weight (Mw) and the ratio of Mw to Mn (number average molecular weight) are used to characterize the molecular weight distribution.

The catalysts of this invention gave good productivities and high molecular weight polymers, as evidenced by very low MI values, and Catalysts VI and VII did so even at higher temperatures (110° C.).

EXAMPLE 5

Synthesis of Bis (2-pyridinoxy) Platinum Dichloride

To a solution of 0.02 moles of 2-hydroxypyridine and 0.02 moles of triethylamine in 50 mL of THF, a solution of 0.01 moles of platinum tetrachloride is added dropwise at 0° C. The solution is then stirred overnight at room temperature. After filtration, the THF solution is evaporated and the product is extracted from the residue. Polymers may be produced using the catalyst by following the procedure of Example 4.

EXAMPLE 6

Synthesis of (2-Pyridinoxy) (Cyclopentadienyl) Vanadium Dichloride

To a solution of 0.002 moles of cyclopentadienyl vanadium trichloride in 50 mL of ether a solution of 2-hydroxy pyridine (0.002 moles) and triethylamine (0.002 moles) in 50 mL of ether is added at 0° C. The solution is stirred overnight. The product is recovered from the ether filtrate. An α-olefin polymer may be produced using the catalyst in accordance with the procedure of Example 4.

EXAMPLE 7

Synthesis of (8-Quinolinoxy) (Cyclopentadienyl) Niobium Trichloride

A solution of 0.01 moles of the lithium salt of 8-hydroxyquinoline in 30 mL of tetrahydrofuran (prepared as described in Example 3) is added dropwise to a solution of 0.01 moles of cyclopentadienyl niobium tetrachloride in 50 mL of tetrahydrofuran at −78° C. After warming to room temperature and stirring overnight, the suspension is filtered and the solvent evaporated under vacuum. The product is recovered by extraction with toluene and then isolated by evaporating the toluene. Polymers may be produced using this catalyst by following the procedure of Example 4.

EXAMPLE 8

Synthesis of (8-Quinolinoxy) Chromium Dichloride

A solution of 0.01 moles of the lithium salt of 8-hydroxyquinoline (prepared as described in Example 3) in 50 mL of tetrahydrofuran is added dropwise to a solution of 0.01 moles of chromium trichloride in 50 mL of tetrahydrofuran at −78° C. After warming to room temperature and stirring overnight, the suspension is filtered and the solvent evaporated under vacuum. The product is recovered from the solids by extraction with toluene and then isolated by evaporating the toluene. Polymers may be produced using this catalyst by following the procedure of Example 4.

EXAMPLE 9

Synthesis of bis(2-Pyridinoxy) Tungsten Tetrachloride

A solution of 0.01 moles of tungsten hexachloride in 20 mL tetrahydrofuran (THF) is added to a solution of 0.02 moles of 2-hydroxypyridine and 0.02 moles of triethylamine in 50 mL THF at 0° C. The mixture is stirred while warming to room temperature, then stirred overnight. The mixture is then filtered and the THF evaporated under vacuum. The product is extracted from the residue with toluene and then recovered by evaporating the toluene. A polymer may be prepared by using the catalyst in accordance with the procedure described in Example 4.

We claim:

1. A catalyst comprising units of the formula:

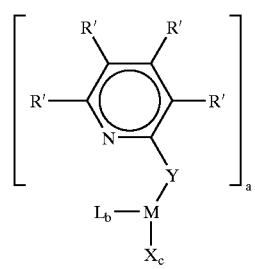

where Y is, —S—, —N—, —P—,
                  |      |
                  R      R -continued

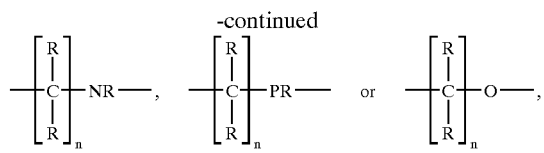

where each R is independently hydrogen, $C_{1-6}$ alkyl, or $C_{6-14}$ aryl;

where each R' is independently R, $C_{1-6}$ alkoxy, $C_{7-20}$ alkaryl, $C_{7-20}$ aralkyl, halogen, or $CF_3$;

where M is a Group 3 to 10 metal;

where each X is independently halogen, $C_{1-6}$ alkyl, $C_{6-14}$ aryl, $C_{7-20}$ alkaryl, $C_{7-20}$ aralkyl, $C_{1-6}$ alkoxy, or

L is X, cyclopentadienyl, $C_{1-6}$ alkyl-substituted cyclopentadienyl, fluorenyl, indenyl, or

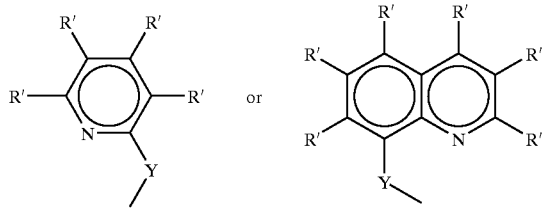

where
n is an integer from 1 to 4;
a is an integer from 1 to 3;
b is an integer from 0 to 2;
the sum of $a+b \leq 3$;
c is an integer from 1 to 6; and
the sum $a+b+c$ equals the oxidation state of M.

2. A catalyst composition suitable for the polymerization of olefins, comprising an activating co-catalyst and a catalyst of the formula:

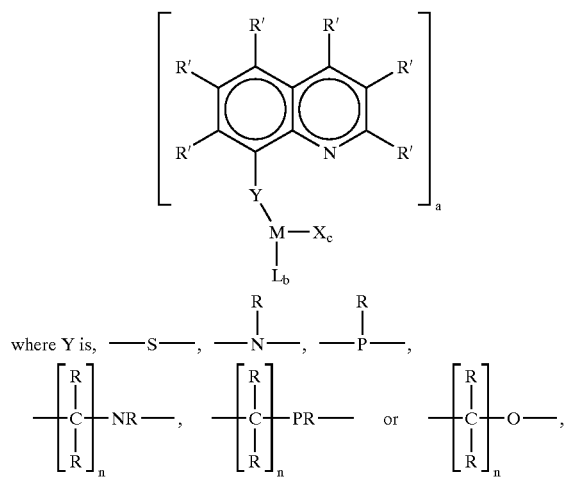

where each R is independently hydrogen, $C_{1-6}$ alkyl, or $C_{6-14}$ aryl;

where each R' is independently R, $C_{1-6}$ alkoxy, $C_{7-20}$ alkaryl, $C_{7-20}$ aralkyl, halogen, or $CF_3$;

where M is a Group 3 to 10 metal;

where each X is independently halogen, $C_{1-6}$ alkyl, $C_{6-14}$ aryl, $C_{7-20}$ alkaryl, $C_{7-20}$ aralkyl, $C_{1-6}$ alkoxy, or

L is X, cyclopentadienyl, $C_{1-6}$ alkyl-substituted cyclopentadienyl, fluorenyl, indenyl,

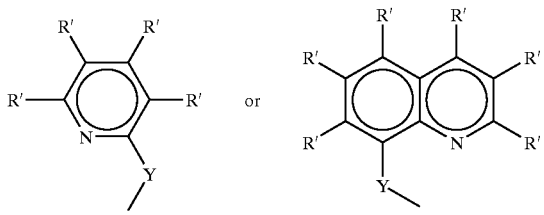

where
n is an integer from 1 to 4;
a is an integer from 1 to 3;
b is an integer from 0 to 2;
the sum of $a+b \leq 3$;
c is an integer from 1 to 6; and
the sum $a+b+c$ equals the oxidation state of M.

3. The catalyst of claim 1, wherein the sum $a+b \leq 2$ when the oxidation state of M is 4 or less and $a+b \leq 3$ when the oxidation state of M is greater than 4.

4. The catalyst of claim 1, wherein X is halogen.

5. The catalyst of claim 1, wherein X is Cl.

6. The catalyst of claim 1, wherein M is a Group 3 to 7 metal.

7. The catalyst of claim 1, wherein M is a Group 4, 5, or 6 metal.

8. The catalyst of claim 1, wherein M is titanium, zirconium, or hafnium.

9. The catalyst of claim 5, wherein M is titanium, zirconium, or hafnium.

10. A catalyst composition useful for the polymerization of olefins, comprising a catalyst of claim 1, and an activating co-catalyst.

11. The catalyst composition of claim 10, wherein said co-catalyst comprises an alumoxane or an aluminum alkyl.

12. The catalyst composition of claim 11, wherein said alumoxane comprises (poly)methylalumoxane, ethylalumoxane, or diisobutylalumoxane.

13. The catalyst composition of claim 10, wherein said co-catalyst is an acid salt containing a non-coordinating inert anion.

14. The catalyst composition of claim 2, wherein X is halogen.

15. The catalyst composition of claim 2, wherein X is Cl.

16. The catalyst composition of claim 2, wherein M is a Group 3 to 7 metal.

17. The catalyst composition of claim 2, wherein M is a Group 4, 5, or 6 metal.

18. The catalyst composition of claim 2, wherein M is titanium, zirconium, or hafnium.

19. The catalyst composition of claim 15, wherein M is titanium, zirconium, or hafnium.

20. The catalyst composition of claim 2, wherein said co-catalyst comprises an alumoxane or an aluminum alkyl.

21. The catalyst composition of claim 20, wherein said alumoxane comprises (poly)methylalumoxane, ethylalumoxane, or diisobutylalumoxane.

22. The catalyst composition of claim 2, wherein said co-catalyst is an acid salt containing a non-coordinating inert anion.

23. The catalyst composition of claim 2, wherein said co-catalyst comprises an alumoxane or an aluminum alkyl and wherein M is titanium.

24. The catalyst composition of claim 2, wherein said co-catalyst is an acid salt containing a non-coordinating inert anon and wherein M is titanium.

25. In a process for the polymerization of olefins in the presence of an olefin polymerization catalyst, the improvement comprising:
selecting as said olefin polymerization catalyst an olefin polymerization catalyst comprising the catalyst of claim 1.

26. In a process for the polymerization of olefins in the presence of an olefin polymerization catalyst, the improvement comprising:
selecting as said olefin polymerization catalyst an olefin polymerization catalyst comprising the catalyst of claim 5.

27. In a process for the polymerization of olefins in the presence of an olefin polymerization catalyst, the improvement comprising:
selecting as said olefin polymerization catalyst an olefin polymerization catalyst comprising the catalyst composition of claim 10.

28. In a process for the polymerization of olefins in the presence of an olefin polymerization catalyst, the improvement comprising:
selecting as said olefin polymerization catalyst an olefin polymerization catalyst comprising the catalyst composition of claim 11.

29. In a process for the polymerization of olefins in the presence of an olefin polymerization catalyst, the improvement comprising:
selecting as said olefin polymerization catalyst an olefin polymerization catalyst comprising the catalyst composition of claim 12.

30. In a process for the polymerization of olefins in the presence of an olefin polymerization catalyst, the improvement comprising:
selecting as said olefin polymerization catalyst an olefin polymerization catalyst comprising the catalyst composition of claim 13.

31. In a process for the polymerization of olefins in the presence of an olefin polymerization catalyst, the improvement comprising:
selecting as said olefin polymerization catalyst an olefin polymerization catalyst comprising the catalyst composition of claim 2.

32. In a process for the polymerization of olefins in the presence of an olefin polymerization catalyst, the improvement comprising:
selecting as said olefin polymerization catalyst an olefin polymerization catalyst comprising the catalyst composition of claim 15.

33. In a process for the polymerization of olefins in the presence of an olefin polymerization catalyst, the improvement comprising:
selecting as said olefin polymerization catalyst an olefin polymerization catalyst comprising the catalyst composition of claim 17.

34. In a process for the polymerization of olefins in the presence of an olefin polymerization catalyst, the improvement comprising:
selecting as said olefin polymerization catalyst an olefin polymerization catalyst comprising the catalyst composition of claim 19.

35. In a process for the polymerization of olefins in the presence of an olefin polymerization catalyst, the improvement comprising:
selecting as said olefin polymerization catalyst an olefin polymerization catalyst comprising the catalyst composition of claim 20.

36. In a process for the polymerization of olefins in the presence of an olefin polymerization catalyst, the improvement comprising:
selecting as said olefin polymerization catalyst an olefin polymerization catalyst comprising the catalyst composition of claim 21.

37. A catalyst comprising units of the formula:

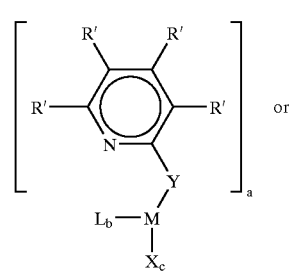

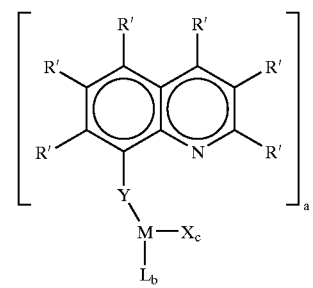

where Y is —O—, where each R is independently hydrogen, $C_{1-6}$ alkyl, or $C_{6-14}$ aryl;

where each R' is independently $C_{1-6}$ alkyl, $C_{6-14}$ aryl, $C_{1-6}$ alkoxy, halogen, or $CF_3$;

where M is zirconium, titanium, and hafnium;

where each X is independently halogen, $C_{1-6}$ alkyl, $C_{1-6}$ alkoxy, or

L is X, cyclopentadienyl, $C_{1-6}$ alkyl-substituted cyclopentadienyl, fluorenyl, indenyl, or

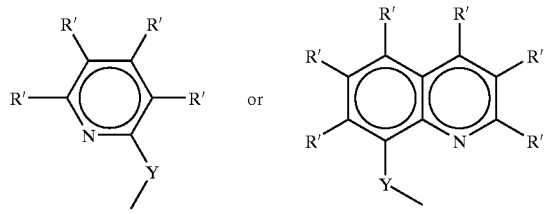

where
n is an integer from 1 to 4;
a is an integer from 1 to 3;
b is an integer from 0 to 2;
the sum of a+b≦3;
c is an integer from 1 to 6; and
the sum a+b+c equals the oxidation state of M.

38. The catalyst of claim 37, wherein the sum a+b≦2 when the oxidation state of M is 4 or less and a+b≦3 when the oxidation state of M is greater than 4.

39. The catalyst of claim 37, wherein X is halogen.

40. The catalyst of claim 37, wherein X is Cl.

41. A catalyst composition useful for the polymerization of olefins, comprising a catalyst of claim 37 and an activating co-catalyst.

42. The catalyst composition of claim 41, wherein said co-catalyst comprises an alumoxane or an aluminum alkyl.

43. The catalyst composition of claim 42, wherein said alumoxane comprises (poly)methylalumoxane, ethylalumoxane, or diisobutylalumoxane.

44. The catalyst composition of claim 41, wherein said co-catalyst is an acid salt containing a non-coordinating inert anion.

* * * * *